United States Patent [19]

Hamilton et al.

[11] Patent Number: 5,662,758

[45] Date of Patent: Sep. 2, 1997

[54] COMPOSITE MATERIAL RELEASABLY SEALABLE TO A TARGET SURFACE WHEN PRESSED THEREAGAINST AND METHOD OF MAKING

[75] Inventors: Peter W. Hamilton, Cincinnati; Kenneth S. McGuire, Wyoming, both of Ohio

[73] Assignee: The Procter & Gamble Company, Cincinnati, Ohio

[21] Appl. No.: 584,638

[22] Filed: Jan. 10, 1996

[51] Int. Cl.⁶ .................................................. B32B 31/00
[52] U.S. Cl. ........................ 156/221; 156/230; 156/235; 156/306.3; 427/208.6
[58] Field of Search ................ 427/208.6; 156/306.3, 156/230, 221, 235

[56] References Cited

U.S. PATENT DOCUMENTS

| | | |
|---|---|---|
| 2,861,006 | 11/1958 | Salditt . |
| 3,312,005 | 4/1967 | McElroy . |
| 3,386,846 | 6/1968 | Lones . |
| 3,592,722 | 7/1971 | Morgan . |
| 3,853,129 | 12/1974 | Kozak . |
| 3,901,237 | 8/1975 | Cepuritis et al. . |
| 3,937,221 | 2/1976 | Tritsch . |
| 3,943,609 | 3/1976 | Egan, Jr. . |
| 3,967,624 | 7/1976 | Milnamow . |
| 4,023,570 | 5/1977 | Chinai et al. . |
| 4,054,697 | 10/1977 | Reed et al. . |
| 4,061,820 | 12/1977 | Magid et al. . |
| 4,181,751 | 1/1980 | Martens et al. . |
| 4,273,889 | 6/1981 | Yamazaki et al. . |
| 4,303,485 | 12/1981 | Levens . |
| 4,336,804 | 6/1982 | Roeder . |
| 4,337,772 | 7/1982 | Roeder . |
| 4,376,440 | 3/1983 | Whitehead et al. . |
| 4,392,897 | 7/1983 | Herrington . |
| 4,397,905 | 8/1983 | Dettmer et al. . |
| 4,410,130 | 10/1983 | Herrington . |
| 4,460,634 | 7/1984 | Hasegawa . |
| 4,519,095 | 5/1985 | Clayton . |
| 4,556,595 | 12/1985 | Ochi . |
| 4,576,850 | 3/1986 | Martens . |
| 4,578,069 | 3/1986 | Whitehead et al. . |
| 4,587,152 | 5/1986 | Gleichenhagen . |
| 4,655,761 | 4/1987 | Grube et al. . |
| 4,699,622 | 10/1987 | Toussant et al. . |
| 4,743,242 | 5/1988 | Grube et al. . |
| 4,946,527 | 8/1990 | Battrell . |
| 4,959,265 | 9/1990 | Wood et al. . |
| 5,080,957 | 1/1992 | Leseman et al. . |
| 5,141,790 | 8/1992 | Calhoun et al. . |
| 5,176,939 | 1/1993 | Shepherd ................... 427/208.6 |
| 5,344,693 | 9/1994 | Sanders . |
| 5,453,296 | 9/1995 | Lauritzen et al. ........... 427/208.6 |
| 5,589,246 | 12/1996 | Calhoun et al. . |

FOREIGN PATENT DOCUMENTS

| | | |
|---|---|---|
| 0 623 332 A1 | 9/1994 | European Pat. Off. . |
| WO9200187 | 9/1992 | WIPO . |

*Primary Examiner*—John J. Gallagher
*Attorney, Agent, or Firm*—Ronald W. Kock

[57] ABSTRACT

A method for making a flexible film having pressure sensitive adhesive protected from inadvertent adherence. The method coats a forming screen with an interconnected layer of pressure sensitive adhesive and places a piece of flexible film in contact with the layer of adhesive. The layer of adhesive preferentially adheres to the piece of flexible film. The forming screen has a plurality of recesses therein. The coating step applies the layer of adhesive without bridging the recesses. Another step forms the piece of flexible film to create a plurality of protrusions extending into the recesses. The plurality of protrusions are registered with the interconnected layer of pressure sensitive adhesive by virtue of using the same screen to transfer adhesive and to form protrusions. The forming screen may be wrapped around a rotating drum and the piece of flexible film may be a portion of a continuous web of flexible film. Preferably, the plurality of protrusions are conical, with a base diameter of 0.015 inches to 0.030 inches, a center-to-center spacing of 0.03 to 0.06 inches, and a protrusion height of 0.004 to 0.012 inches.

10 Claims, 2 Drawing Sheets

COMPOSITE MATERIAL RELEASABLY SEALABLE TO A TARGET SURFACE WHEN PRESSED THEREAGAINST AND METHOD OF MAKING

FIELD OF THE INVENTION

The present invention relates to flexible films coated with pressure sensitive adhesive for releasable sealing to a target surface, and more particularly to such films which have features for preventing premature sticking to a target surface during film positioning thereon. Even more particularly, the present invention relates to flexible films having protrusions formed on an adhesive side which act to space a pressure sensitive adhesive from a target surface until the film is pressed thereagainst. It further relates to a method of making such formed and adhesively coated flexible films.

BACKGROUND OF THE INVENTION

In the art of tapes, labels, and other articles using pressure sensitive adhesive to adhere an adhesive coated surface to a target surface, there has been recognized the problem of premature sticking. That is, before the adhesive coated surface can be properly positioned over a target surface, inadvertent contact of the adhesive with the target surface causes premature sticking at one or more locations, thereby inhibiting proper positioning.

Others have attempted to overcome this problem. For example, in the catamenial field, where it is useful to adhere an absorbent pad to the inside of an undergarment, manufacturers have made it necessary to press the garment against the back of the pad before adhesive contact can occur. Protecting the adhesive from premature contact is achieved by adding strips of foam to the back of the pad, which provide an initial contact surface outwardly from the adhesive surface. The strips of foam act as stand-offs from the adhesive surface. Once the undergarment is positioned properly, it may be pressed into the space between strips of foam. Adhesion to a pressure sensitive adhesive layer fixes the pad in place. Of course, for this approach to work, the undergarment has to be flexible enough to deform around the strips of foam.

U.S. Pat. No. 4,376,440 to Whitehead et al. discloses sanitary napkins having recessed patterns of pressure sensitive adhesives for sticking the napkins to undergarments. A water based emulsion adhesive is suggested. Foam baffles surround pockets into which the adhesive is placed. This invention is limited to target surfaces which deform into the adhesive pockets.

European Patent Application No. 0 623 332 A1 to Lauritzen describes methods for making a sanitary napkin which has a recessed adhesive pattern for attaching it to a user's undergarment. Lauritzen forms depressions in a fluid-impervious barrier film. The depressions create raised areas in the barrier film on the side of the napkin which attaches to the undergarment. Adhesive is placed onto the barrier film side having the raised areas, but only in discrete patterns between the raised areas. The adhesive is at a level below the peaks of the raised areas and is therefore protected by the raised areas from contact with the undergarment. In an alternative, Lauritzen applies adhesive to the tips of the raised areas of the barrier film and then inverts the raised areas to form depressions. The adhesive is thereby conveniently placed in the depressions. Discrete adhesive placement fails to enable a total adhesive seal. The adhesive must be interconnected to achieve such a seal.

Lauritzen notes that the depressions must be formed such that they are strong enough to protect the adhesive from inadvertent contact during shipping and storage, yet are deformable by pressing the undergarment against the barrier film. Lauritzen states that sufficient rigidity is available from 0.03 inch to 0.06 inch thick film. In one embodiment, conical depressions have diameters at their open ends of 0.1 to 0.5 inches and depths of 0.1 to 0.25 inches. Such large depressions and thick film preclude the ability to wind up the fluid-impervious barrier film separately in a compact a roll.

In still another Lauritzen embodiment, a printing device transfers adhesive to a printing belt, which transfers adhesive to a release belt, and then to the barrier film web. This system is used to first print a pattern of discrete patches of adhesive onto the barrier film web. Then the film web is registered with a vacuum plate. When each patch of adhesive is disposed above a recess in the forming plate, vacuum forms adhesive containing depressions. Because of registration requirements, the invention is believed limited to relatively large depressions.

U.S. Pat. No. 4,959,265 to Wood et al. discloses an adhesively coated substrate having bluntly pointed stems protruding beyond a layer of pressure sensitive adhesive. The back of this substrate may be bonded to a sanitary napkin. The napkin may then be installed onto a foraminous fabric by pressing to force the stems to penetrate the fabric to a depth where the fabric contacts the adhesive. "By penetrating fabric, the stems significantly reinforce the adhesion of the fastener". The stems "should be resistant to compression and bending, even thought they may be quite supple." "The backing with its stems preferably is formed from a tough thermoplastic resin by cast molding or extrusion molding." The stems protrude 20 microns to 3 mm above the adhesive level, depending on the coarseness of the fabric to be penetrated. The adhesive area is preferably between 3 and 30 times the area occupied by the stems. Smooth rigid surfaces are obviously inoperable with Wood et al.

U.S. Pat. No. 5,344,693 to Sanders discloses a substrate having a plurality of non-interconnecting spacing means extending outwardly from an adhesive coated surface to space the surface from another surface until the surfaces are pressed together. The spacing means of Sanders is non-deformable. Sanders points out that prior art discloses deformable spacing means where force is applied to a surface of interest, but that his spacers are non-deformable so that spacing will be maintained when the substrate is stored in a roll. The spacing members are spaced not more than 80 times the dimension of each spacer. Sanders discusses this invention for use with reclosable bags. Sanders, like Wood et al., would not be compatible with smooth rigid target surfaces.

U.S. Pat. No. 5,141,790 to Calhoun et al. discloses one-time repositionable pressure sensitive tapes with an adhesive coated surface having clumps of particles spaced out on the adhesive to keep the adhesive from touching a target surface during positioning and until the sheet is pressed against the target surface. The particles are smaller than the thickness of the adhesive layer so that when pressed, the particles sink below the surface of the adhesive and no longer provide their spacing function. Thus, Calhoun et al. is intended for only one use.

U.S. Pat. No. 4,061,820 to Magid et al. discloses a foam with cells. The foam is compressed to open cell cavities at the foam surface so that pressure sensitive adhesive can be applied to the open cells. When the foam is released, the cells close and hide the adhesive. When the foam is pressed, the cells bring pressure sensitive adhesive to the surface for sticking the foam to a target surface. This is believed to be both an expensive and significantly thick solution to the problem.

The prior art has focused on the use of stand-offs with pressure sensitive adhesives primarily in the area of sanitary napkins. However, different solutions are needed for flexible films intended to be stuck to themselves or to smooth rigid surfaces.

The prior art methods for applying adhesive to surfaces having stand-offs are aimed at surfaces having large sized stand-offs and/or large spacing between stand-offs. What is missing is a method of applying pressure sensitive adhesive to a flexible film with very small stand-offs and which are closely spaced, where the registration of stand-offs and the adhesive pattern is critical.

OBJECTS OF THE INVENTION

It is an object of the present invention to provide a composite material having a recessed pressure sensitive adhesive layer and collapsible protrusions which serve as stand-offs to prevent premature sticking to a wide variety of rigid and resilient target surfaces, wherein the collapsible protrusions are small and closely spaced for releasable sealing of the composite material to such surfaces or even to itself.

It is another object of the present invention to provide a composite material having a recessed pressure sensitive adhesive layer and collapsible protrusions which serve as stand-offs, wherein the composite material is relatively thin and therefore inexpensive and capable of being wound onto compact rolls for storage and convenient packaging, yet resistance to total collapse of protrusions is sufficient to prevent premature collapse before the composite material is unwound from a roll for use.

It is still another object of the present invention to provide a composite material having a recessed pressure sensitive adhesive layer and collapsible protrusions which serve as stand-offs, wherein a continuous, leak resistant, adhesive seal may be made by virtue of an interconnected adhesive pattern between protrusions.

It is a further object of the present invention to provide a method for making a composite material having a recessed pressure sensitive adhesive layer and collapsible protrusions, without regard for registration of protrusions and an adhesive pattern, wherein the method is capable of automated continuous motion or indexing motion for a continuous web format.

SUMMARY OF THE INVENTION

A flexible film has thermoformed protrusions between a grid of pressure sensitive adhesive. The protrusions prevent adhesion of the film to itself or to another surface until the film is pressed against the target surface. Pressing collapses the protrusions locally to enable the adhesive to contact and stick to the target surface. The adhesive has limited aggressiveness so that the film may be peeled away from the target surface such that the adhesive stays with the film. Even two coated film surfaces may be pressed together to form a seal, yet they may later be peeled apart.

Articles may be wrapped with the film of the present invention, thereby providing a competitive substitute for films that supposedly cling to contact surfaces. Having an adhesive allows a film to stick to plastic containers. Plain plastic films do not stick to such containers. The film could also be used as a tape, which does not stick until pressed.

In one aspect of the present invention, a method for making a flexible film having pressure sensitive adhesive protected from inadvertent adherence coats a forming screen with an interconnected layer of pressure sensitive adhesive and places a piece of flexible film in contact with the interconnected layer of pressure sensitive adhesive on the top surface of the forming screen. The interconnected layer of pressure sensitive adhesive preferentially adheres to the piece of flexible film. The forming screen has a top surface and the top surface has a plurality of recesses therein. The coating step applies the interconnected layer of pressure sensitive adhesive to the top surface without bridging the recesses.

Another step forms the piece of flexible film to create a plurality of protrusions extending into the recesses of the forming screen. The piece of flexible film has an adhesive side and a non-adhesive side. The plurality of protrusions are registered with the interconnected layer of pressure sensitive adhesive on the adhesive side. A final step removes together the piece of flexible film and the layer of interconnected pressure sensitive adhesive from the forming screen.

The forming screen may be wrapped around a rotating drum and the piece of flexible film may be a portion of a continuous web of flexible film, such that the method is a continuous process. Also, the forming screen may be coated with a release material prior to applying the layer of interconnected pressure sensitive adhesive.

The plurality of protrusions may be formed by applying heat to the non-adhesive side of the piece of flexible film and by applying vacuum to the adhesive side of the piece of flexible film. Alternatively, the plurality of protrusions may be formed by applying heated compressed gas to the non-adhesive side of the piece of flexible film while the piece of flexible film rests against the forming screen. In yet another alternative method step, the plurality of protrusions may be formed by mechanically embossing the piece of flexible film into the recesses of the forming screen from the non-adhesive side of the piece of flexible film. Such thermoforming and cold forming methods are well known in the art.

The plurality of protrusions are preferably formed in the piece of flexible film to have a domed shape and each protrusion has a height less than a diameter of the protrusion, so that when pressed, the plurality of protrusions will collapse in a direction substantially perpendicular to a plane of the flexible film.

Each of the plurality of recesses of the forming screen are circular and have a base diameter of about 0.025 inches and depth of about 0.006 inches to 0.012 inches. The plurality of recesses are substantially equally spaced about 0.050 inches apart in an equilateral triangular pattern.

In another aspect of the present invention, a composite material is releasably sealable to a target surface. The composite material comprises a piece of flexible film and pressure sensitive adhesive. The flexible film has an adhesive side and a non-adhesive side. The adhesive side is formed to have a plurality of conical protrusions separated by valleys. The plurality of conical protrusions have outermost ends and a base diameter of 0.015 inches to 0.030 inches, a center-to-center spacing of 0.03 to 0.06 inches, and a protrusion height of 0.004 to 0.012 inches. The valleys are interconnected between the plurality of protrusions. Each of the plurality of protrusions has a domed shape. Each domed shape has a height above the adhesive side of the piece of flexible film less than a diameter of the domed shape. When pressed, the protrusions collapse in a direction substantially perpendicular to the adhesive side without blocking the coating of pressure sensitive adhesive from contact with the target surface. The pressure sensitive adhesive adheres preferentially to the adhesive side of the piece of flexible film and is peelable from the target surface.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
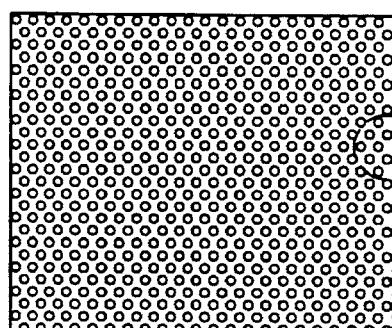
FIG. 1 is a top plan view of a preferred embodiment of the composite material of the present invention, disclosing a piece of flexible film having thermoformed truncated conical protrusions between a grid of pressure sensitive adhesive.
Figure 2:
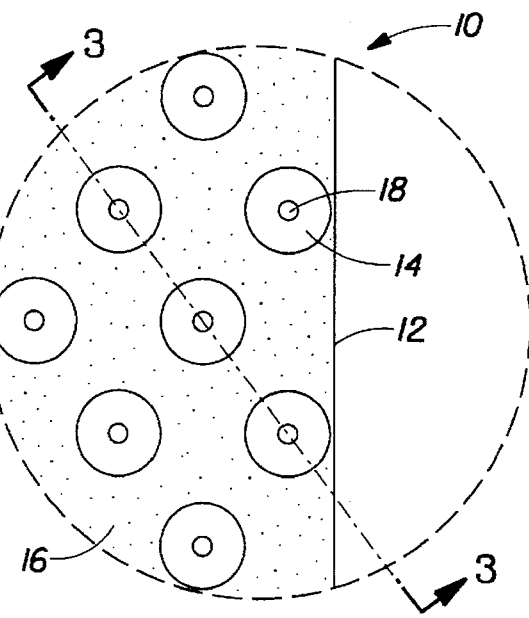
FIG. 2 is an enlarged partial top plan view thereof, showing a nested pattern of thermoformed truncated conical protrusions, spaced apart with a layer of adhesive in the valleys between protrusions.

Referring now to the drawings, and more particularly to FIGS. 1–4, there is shown a preferred embodiment of the present invention, which provides the composite film and is generally indicated as 10. Composite film 10 includes a piece of flexible film 12 having protrusions 14 and a layer of pressure sensitive adhesive 16 located between protrusions 14. Protrusions 14 are preferably conical in shape with truncated or domed outermost ends 18. Protrusions 14 are preferably equally spaced in an equilateral triangular pattern, all facing the same direction. They are preferably spaced center to center a distance approximately two protrusion diameters. Protrusions 14 have heights which are preferably less than their diameters, so that when they collapse, they collapse along an axis which is substantially perpendicular to a plane of film 12. This mode of collapse avoids protrusions 14 folding over and blocking adhesive from contact with a target surface.

Figure 3:
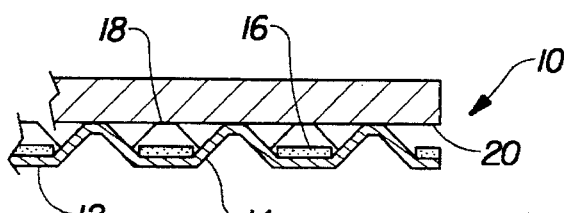
FIG. 3 is a sectioned elevation view thereof, taken along section line 3—3 of FIG. 2, showing the protrusions acting as stand-offs from an adhesive layer between protrusions, such that a target surface contacting the outermost ends of the protrusions does not contact the adhesive layer.
Figure 4:
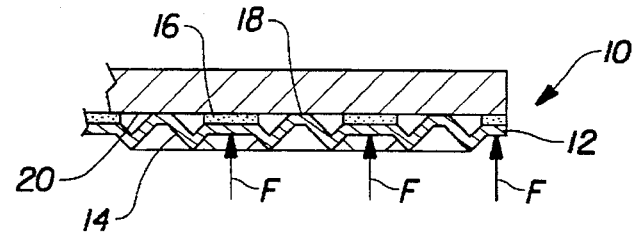
FIG. 4 is a sectioned elevation view thereof, similar to FIG. 3, showing the effect of pressing the dimpled composite material against the target surface, such that protrusions collapse and allow the adhesive layer between protrusions to contact the target surface.

FIG. 3 shows a target surface 20, which may be smooth and rigid, being spaced away from layer of pressure sensitive adhesive 16 by outermost ends 18 of protrusions 14. FIG. 4 shows target surface 20 contacting layer of pressure sensitive adhesive 16 alter protrusions 14 have partially inverted on themselves under pressure applied to the non-adhesive side of flexible film 12, as indicated by force F.

In a particularly preferred embodiment, conical protrusions 14 have a base diameter of about 0.015 inches to about 0.030 inches, and more preferably about 0.025 inches. They also have a center-to-center spacing of from 0.03 to 0.06 inches, and more preferably about 0.05 inches, and a protrusion height of about 0.004 inches to 0.012 inches, and more preferably about 0.006 inches. The preferred film material is 0.001 inch nominal thickness low density polyethylene. Preferred layer of pressure sensitive adhesive 16 is preferably latex about 0.001 inch thick. The size and spacing of protrusions is optimized to provide a continuous adhesive path for fluid tight seals, but without generating a film that is easily stretched. Stretched film results in residual forces parallel to the plane of adhesive contact, which may cause the weak adhesive bond to break. The larger and more closely centered the protrusions, the greater the likelihood of stretch occurring. A limiting factor in reducing the size and spacing of protrusions is the ability to apply adhesive to the film without causing the adhesive to bridge recesses in the forming screen and thereby cause adhesive to coat the protrusions.

Figure 5:
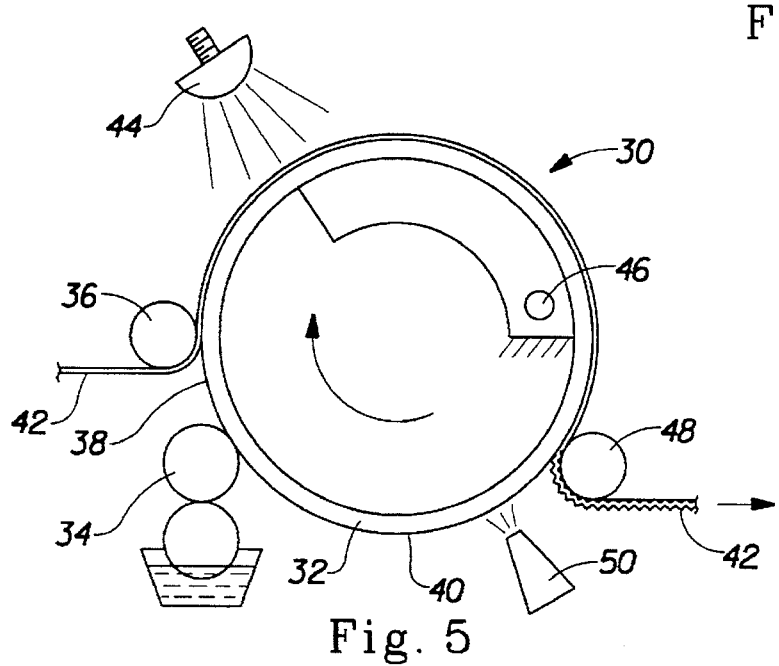
FIG. 5 is a side elevation view of a method for making the composite material of the present invention, disclosing a continuous web of flexible film entering a thermoforming drum, which has an external heat source and internal vacuum manifold, wherein adhesive is applied to the drum and transferred to the film prior to thermoforming protrusions in the film.

FIG. 5 shows an automated process for making composite material 10, generally indicated as 30. A forming screen 32 is curved to form a drum. A pressure sensitive adhesive source and application system 34 is positioned upstream of an infeed idler roll 36. Adhesive application system 34 deposits about a 0.001 inch thick coating of pressure sensitive adhesive 38 onto the outer surface 40 of forming screen drum 32. Outer surface 40 is treated to have a low surface energy so that adhesive 38 will not readily wet it. Automated process 30 has a web of film 42 threaded between infeed idler roll 36 and forming screen drum 32. In this process, film web 42 is deposited on top of layer of pressure sensitive adhesive 38. Film web 42 is preferably treated to bond well to layer of pressure sensitive adhesive 38. As drum 32 rotates past idler roll 36, heat from radiant heat source 44 softens film web 42 for thermoforming. Meanwhile, layer of pressure sensitive adhesive 38 is transferred from the drum to the film web. A vacuum manifold 46 operates with drum 32 so as to suck film 42 around layer of pressure sensitive adhesive 38 and into recesses in forming screen drum 32 for forming protrusions similar to protrusions 14.

As forming screen 32 rotates, vacuum thermoforming is completed, and film web 42 is thereafter cooled and discharged around discharge idler roll 48. Automated process 30 may also have a sprayer 50 located upstream of adhesive application system 34. Sprayer 50 is preferably used for applying a release agent to outer surface 40 so that adhesive 38 will be preferentially attracted to film web 42. Alternatively, a permanent teflon coating applied to outer surface 40 may avoid the need for sprayer 50.

Alternatives to heat and vacuum for forming protrusions in a film are well known in the art. For example, by applying heated compressed gas to the non-adhesive side of the web of flexible film while the web of flexible film rests against said forming screen, protrusions may be created. Also, mechanically embossing the film against the forming screen is possible.

Figure 6:
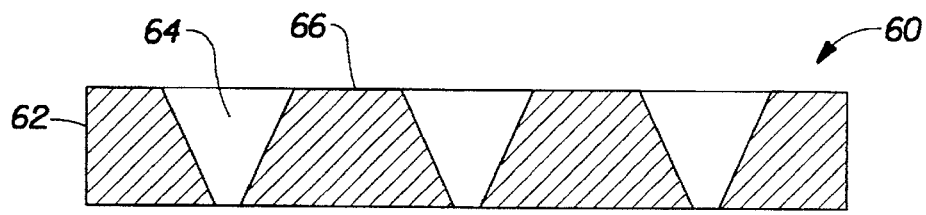
FIG. 6 is a sectioned elevation view of a forming screen used for making the composite material of the present invention, disclosing tapered recesses for protrusion forming.

FIGS. 6–10 show steps of a preferred laboratory method of making pieces of composite material 10, generally indicated as 60. As shown in FIG. 6, method 60 utilizes forming screen 62, which has a plurality of conical recesses 64, about 0.025 inches in diameter at the larger end. Recesses 64 are preferably photo-etched into forming screen 62, which is a stainless steel sheet, about 0.006 inches to 0.012 inches thick. Forming screen 62 has a top surface 66, which is teflon coated to provide release properties for an adhesive.

Figure 7:
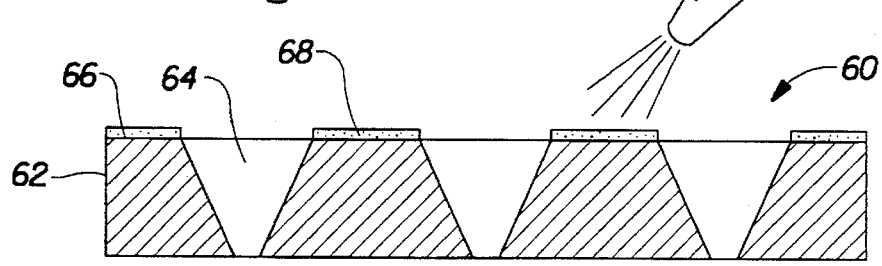
FIG. 7 is a sectioned elevation view thereof, showing pressure sensitive adhesive sprayed onto a top surface of the forming screen, such that the adhesive layer does not bridge the recesses in the top surface.

FIG. 7 shows a water based latex emulsion 68 sprayed onto top surface 66 by sprayer 70. Latex emulsion 68 is a pressure sensitive adhesive when dried. Drying is achieved by application of warm air or radiant heat for about 30 seconds. The latex emulsion coating does not bridge the 0.025 inch diameter recesses, but instead remains only on top surface 66 between recesses. Applying a low level vacuum through recesses 64 during spraying of the latex emulsion onto top surface 66 helps to ensure no bridging of recesses 64.

Figure 8:
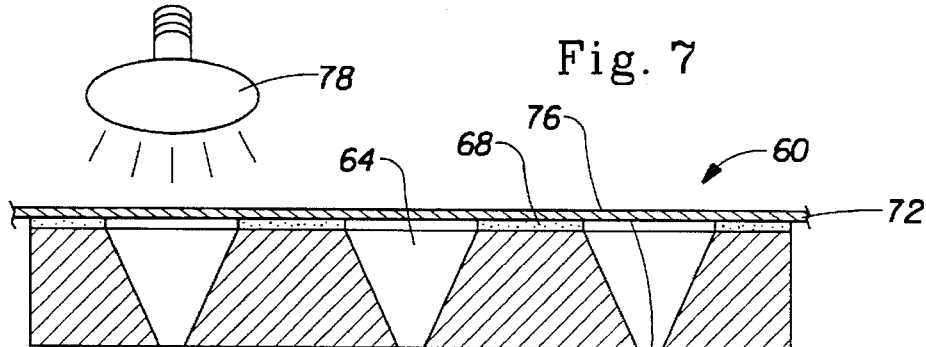
FIG. 8 is a sectioned elevation view thereof, showing a piece of film laid on top of the layer of pressure sensitive adhesive and being exposed to heat from an infrared source on the side opposite the adhesive side.

FIG. 8 shows a piece of flexible film 72, made of 0.001 inch nominal thickness low density polyethylene, laid on top of dried latex emulsion 68. The actual film thickness may vary from 0.0005 inch to 0.0015 inch. Preferably, piece of flexible film 72 has an adhesive side 74 which has been corona treated for maximum adhesion to pressure sensitive adhesive 68. It also has a non-adhesive side 76 facing outward. In order to initiate thermoforming of piece of flexible film 72, the film is heated by an infrared heating lamp 78 from non-adhesive side 76. Heating occurs for approximately 60 seconds until piece of flexible film 72 is heated to about 200° F. to 300° F. Alternatively, hot air could be used to heat piece of flexible film 72.

Figure 9:
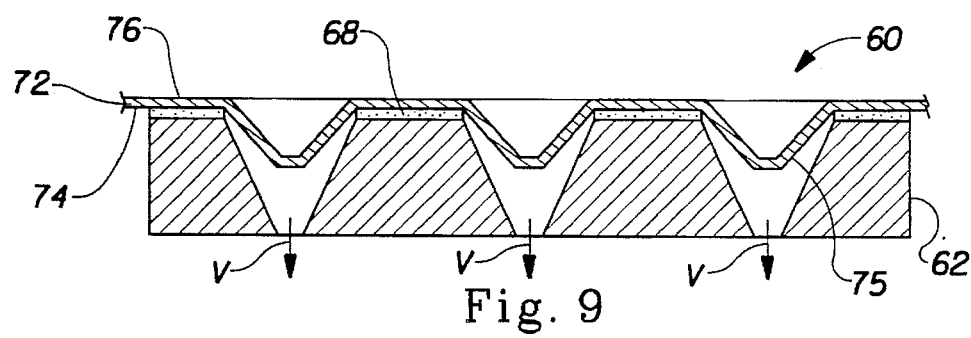
FIG. 9 is a sectioned elevation view thereof, showing vacuum applied through the recesses to form the heated film into the recesses to form protrusions in the film between the pattern of adhesive.
Figure 10:
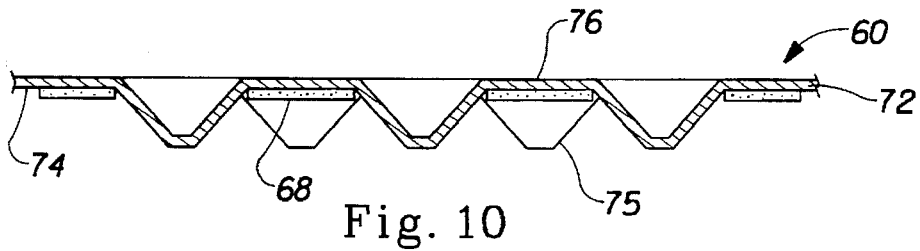
FIG. 10 is a sectioned elevation view thereof, showing the forming screen removed, leaving the adhesive layer attached to the film between the protrusions.

Immediately after film heating, as shown in FIG. 9, vacuum V is applied from a source not shown to recesses 64 at their open ends. Vacuum V is approximately 20 inches of mercury. Vacuum V sucks portions of softened flexible film 72 lying above recesses 64 down into recesses 64 to form protrusions 75. When piece of flexible film 72 is allowed to cool, it is removed from forming screen 62, as shown in FIG. 10. Because of preferential adhesion, pressure sensitive adhesive 68 stays attached to piece of flexible film 72. The piece of flexible film is thereby thermoformed to generate conical protrusions with truncated cone or domed outermost ends. The outermost ends extend approximately 0.003 inches to 0.011 inches beyond the surface of layer of pressure sensitive adhesive 68, depending on the height of the protrusions. Because the same forming screen is used to transfer the adhesive to the film as is used to form the protrusions, the adhesive pattern is conveniently registered with the protrusions. Since the top surface 66 of forming screen 62 is continuous except for recesses 64, the adhesive pattern is totally interconnected.

It is believed that the protrusion size and spacing, the film flexural modulus, and the film thickness determine the stiffness of the protrusions to collapse over a unit area. It is desirable to provide a stiffness which is sufficient to withstand a pressure of 0.4 pounds per square inch without collapsing protrusions to where the adhesive contacts a target surface. This minimum resistance to collapse enables the composite material to be wound onto a roll without damage for compact packaging purposes. A composite material having the most preferred dimensions is believed to provide the desired stiffness. While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A method for making a flexible film having pressure sensitive adhesive protected from inadvertent adherence, said flexible film being stickable to a target surface only when pressed thereagainst, said method comprising the steps of:

a) coating a forming screen with a pressure sensitive adhesive, said forming screen having a top surface, said top surface having a plurality of recesses therein, said coating step applying said pressure sensitive adhesive to said top surface without bridging said recesses;

b) placing a piece of flexible film in contact with said pressure sensitive adhesive on said top surface of said forming screen, said pressure sensitive adhesive preferentially adhering to said piece of flexible film;

c) forming said piece of flexible film to create a plurality of protrusions extending into said recesses of said forming screen, said plurality of protrusions being registered with said pressure sensitive adhesive; and d) removing said piece of flexible film together with said pressure sensitive adhesive from said forming screen.

2. The method of claim 1 wherein said forming screen is wrapped around a rotating drum and said piece of flexible film is a portion of a continuous web of flexible film.

3. The method of claim 1 wherein said piece of flexible film has an adhesive side and a non-adhesive side and said plurality of protrusions are formed by heat applied to said non-adhesive side of said piece of flexible film and by vacuum applied to said adhesive side of said piece of flexible film.

4. The method of claim 1 wherein said piece of flexible film has an adhesive side and a non-adhesive side and said plurality of protrusions are formed by applying heated compressed gas to said non-adhesive side of said piece of flexible film while said adhesive side of said piece of flexible film rests against said forming screen.

5. The method of claim 1 wherein said piece of flexible film has an adhesive side and a non-adhesive side and said plurality of protrusions are formed by mechanically embossing of said piece of flexible film into said recesses of said forming screen from said non-adhesive side of said piece of flexible film.

6. The method of claim 1 further comprising the step of coating said forming screen with a release material prior to applying said layer of pressure sensitive adhesive.

7. A method for making a flexible film having pressure sensitive adhesive protected from inadvertent adherence, said flexible film being stickable to a target surface only when pressed thereagainst, said method comprising the steps of:

a) coating a forming screen with a pressure sensitive adhesive, said forming screen having a top surface, said top surface having a plurality of recesses therein, said coating step applying said pressure sensitive adhesive to said top surface without bridging said recesses;

b) placing a piece of flexible film in contact with said pressure sensitive adhesive on said top surface of said forming screen, said pressure sensitive adhesive preferentially adhering to said piece of flexible film;

c) forming said piece of flexible film to create a plurality of protrusions extending into said recesses of said forming screen, said plurality of protrusions having a closely spaced pattern which provides sufficient collapse resistance while permitting minimal film thickness for compact roll winding, said plurality of protrusions being registered with said pressure sensitive adhesive, wherein each of said plurality of protrusions is formed in said piece of flexible film to have a domed shape having a height less than a diameter of said protrusion, so that when pressed, said plurality of protrusions will collapse in a direction substantially perpendicular to said piece of flexible film to avoid blocking said pressure sensitive adhesive from contact with said target surface; and d) removing said piece of flexible film together with said pressure sensitive adhesive from said forming screen.

8. The method of claim 7 wherein each of said plurality of recesses of said forming screen are substantially equally spaced about 0.050 inches apart in an equilateral triangular pattern.

9. The method of claim 7 wherein each of said plurality of recesses of said forming screen are circular and have a base diameter of about 0.025 inches and depth of about 0.008 inches.

10. A method for making a flexible film having pressure sensitive adhesive protected from inadvertent adherence, said flexible film being stickable to a target surface only when pressed thereagainst, said method comprising the steps of:

a) coating a forming screen with a pressure sensitive adhesive, said forming screen having a top surface, said top surface having a plurality of recesses therein, said coating step applying said pressure sensitive adhesive to said top surface without bridging said recesses;

b) placing a piece of flexible film in contact with said pressure sensitive adhesive on said top surface of said forming screen, said pressure sensitive adhesive preferentially adhering to said piece of flexible film;

c) forming said piece of flexible film to create a plurality of protrusions extending into said recesses of said forming screen, said plurality of protrusions being registered with said pressure sensitive adhesive, wherein said pressure sensitive adhesive forms an interconnected layer in valleys between said plurality of protrusions and said piece of flexible film is continuously sealable to said target surface in a leak resistant manner by virtue of said pressure sensitive adhesive being an interconnected layer; and d) removing said piece of flexible film together with said pressure sensitive adhesive from said forming screen.

* * * * *